United States Patent [19]

Tschang et al.

[11] 4,266,030

[45] May 5, 1981

[54] MACROPOROUS POLYMERIC CARRIER FOR COVALENTLY BINDING PROTEINS, ITS PREPARATION AND ITS USE FOR FIXING ACTIVE PROTEINS

[75] Inventors: Chung-Ji Tschang, Frankenthal; Heinrich Klefenz, Hochdorf-Assenheim; Axel Sanner, Frankenthal, all of Fed. Rep. of Germany

[73] Assignee: BASF Aktiengesellschaft, Fed. Rep. of Germany

[21] Appl. No.: 146,400

[22] Filed: May 5, 1980

Related U.S. Application Data

[62] Division of Ser. No. 57,010, Jul. 12, 1979.

[30] Foreign Application Priority Data

Aug. 7, 1978 [DE] Fed. Rep. of Germany ....... 2834539

[51] Int. Cl.$^3$ .......................... C12N 11/08; C08J 9/00
[52] U.S. Cl. ........................................ 435/180; 260/8; 435/188; 521/53; 521/145; 521/150
[58] Field of Search ................... 435/180, 188; 260/8; 521/53, 145, 150

[56] References Cited

U.S. PATENT DOCUMENTS 3,326,866  6/1967  Haag ............................. 521/53
3,458,976  8/1969  Hollis ........................... 521/147

FOREIGN PATENT DOCUMENTS 2621974  11/1977  Fed. Rep. of Germany.
1257263  12/1971  United Kingdom.

OTHER PUBLICATIONS

Helv. Chim. Acta, vol. XL (1957), pp. 61–68.

*Primary Examiner*—Morton Foelak
*Attorney, Agent, or Firm*—Keil & Witherspoon

[57] ABSTRACT

A macroporous crosslinked styrene resin, used as a carrier for covalently binding proteins, which resin contains isocyanate, thioisocyanate or aldehyde groups as protein-binding groups and may or may not contain sulfonic acid groups—which may also be in the form of the sodium salt or of sulfonic acid amide groups—as hydrophilic groups.

The carrier according to the invention is prepared from a sulfochlorinated macroporous crosslinked styrene resin by reacting the sulfonic acid chloride groups with an $\alpha,\omega$-diamino compound, with hydrazine or with an $\alpha,\omega$-diamino-diether, converting any sulfonic acid chloride groups which may still be present to free sulfonic acid groups, their sodium salt or a sulfonamide group, and then reacting the terminal amino groups with phosgene, thiophosgene or a diisocyanate in order to produce the binding groups, which in turn fix a biologically active protein by covalent bonds.

3 Claims, No Drawings

MACROPOROUS POLYMERIC CARRIER FOR COVALENTLY BINDING PROTEINS, ITS PREPARATION AND ITS USE FOR FIXING ACTIVE PROTEINS

This is a division of application Ser. No. 57,010, filed July 12, 1979, allowed.

The present invention relates to the binding of active proteins to porous polymers.

For the purposes of the invention, proteins are biologically active substances, preferably enzymes. Such substances are used, inter alia, in medical analysis and in the preparation of pharmaceutical products, of optically active substances and of nutrients, for example isoglucose. The advantages of using bound proteins are their reusability, the ease with which they can be separated from the substrate or from its solution, their frequently greater stability compared to the soluble form, the avoidance of contamination of the reaction products, and the capability of carrying out continuous reactions in columns or similar reactors.

A plurality of possible ways of immobilizing biologically active substances has been disclosed. However, as yet no process for binding or immobilizing biologically active substances has been found which is substantially free from significant shortcomings. For example, adsorptive and ionic binding in general do not meet all requirements in respect of strength and durability. Embedding a biologically active substance in a polymeric carrier also has certain disadvantages. In this process, the carrier is polymerized in the presence of the biologically active substance, as a result of which part of the biological activity is as a rule lost.

In the commonest processes for binding a biologically active substance, a covalent bond to the carrier is formed. For this method, again, a plurality of processes has been disclosed. A comprehensive survey is to be found, for example, in Methods in Enzymology, volume XLIV: Immobilized Enzymes, Academic Press, 1976. In these cases, again, it is known that the carriers used hitherto suffer from numerous shortcomings.

Carriers based on polysaccharides, eg. cellulose, starch, dextran, agarose and their derivatives, are not resistant to bacterial or enzymatic degradation, in most cases possess unsatisfactory hydrodynamic properties, and in some instances are exceptionally expensive. Inorganic carriers, eg. alumina, silica gel, various ceramic materials or porous glass on the other hand present considerable difficulties in obtaining the required pore diameter and pore volume. Furthermore, in the case of inorganic carriers the attachment of reactive groups, ie. of groups which covalently bind biologically active substances, is in some cases very difficult and expensive. Polymeric carriers used hitherto are predominantly employed in the form of gels (cf., for example, German Laid-Open Applications DOS No. 2,260,185 and DOS No. 2,263,289) and foams (cf., for example, German Published Application DAS No. 1,642,596, German Laid-Open Applications DOS No. 2,365,854, DOS No. 2,612,138, DOS No. 2,625,471 and DOS No. 2,625,544 and U.S. Pat. No. 3,939,574), and exhibit unsatisfactory hydrodynamic behavior, ie. the permeation rates are limited and, because of the unsatisfactory mechanical properties, cannot be increased.

Polymeric carriers with isocyanate or aldehyde groups as binding groups are described, for example, in German Laid-Open Applications DOS No. 2,621,974 and DOS No. 1,915,970, but again the disadvantages mentioned above apply to the said carriers.

It is an object of the present invention to provide porous organic polymeric carriers which avoid the known disadvantages and which are capable of covalently binding biologically active substances, whilst substantially retaining their activity, so that the biologically active preparations produced in the reaction are stable under the conventional use conditions. The preparations are designed to have a high activity and to be suitable, by virtue of their hydrodynamic properties, for operation in a column.

We have found that this object is achieved by providing a macroporous crosslinked styrene resin as the carrier for covalently binding proteins, which carrier contains isocyanate, thioisocyanate or aldehyde groups as protein-binding groups and may or may not contain sulfonic acid groups—which may also be in the form of the sodium salt or of sulfonic acid amide groups—as hydrophilic groups.

The carrier according to the invention is prepared from a sulfochlorinated macroporous crosslinked styrene resin which contains from 1 to 4.5, preferably from 2 to 4, milliequivalents/g of sulfonic acid chloride groups and has a pore size of $2 \times 10^{-5}$–$15 \times 10^{-5}$ mm, preferably $5 \times 10^{-5}$–$13 \times 10^{-5}$ mm.

The principle of preparing such styrene resins is known to those skilled in the art and is described in the literature by, for example, Brutskus et al. in Coll. J. USSR 34 (1972), 438–442.

The preparation of the styrene resin used according to the invention employs from 97 to 50, preferably from 80 to 60, % by weight of styrene and from 3 to 50, preferably from 7 to 25, % by weight of divinylbenzene, with or without from 1 to 25% by weight of ethylvinylbenzene and with or without an additional 1 to 10% by weight, based on the total weight, of a comonomer from the group comprising 2- and 4-vinylpyridine, N-vinylimidazole, N-vinylpyrrolidone, hydroxypropyl acrylate and tert.-butyl acrylate; the polymerization is carried out in the conventional manner.

The suspension polymerization process is preferred, and as a rule beads having a diameter of from 0.2 to 1.5 mm are obtained. Amongst the above comonomers, ethylvinylbenzene is of particular interest since technical-grade divinylbenzene, should the latter for example be used, contains from 1 to 50% by weight of ethylvinylbenzene, ie. the carrier according to the invention may contain up to 25% by weight of ethylvinylbenzene as copolymerized units.

Pore-forming agents used in the polymerization are advantageously alkanes of 7 to 12 carbon atoms, preferably n-octane or an alkane mixture obtainable by conventional methods, for example a relatively high-boiling petroleum ether. The amount of the pore-forming agent used is from 50 to 140, preferably from 80 to 120, % by weight based on the total weight of the monomers employed.

Even if comonomers are copolymerized, polymers having the above pore sizes are obtained. Corresponding to the pore sizes stated, the pore volumes measured are from 0.5 to 2 cm$^3$/g, preferably from 0.7 to 1.5 cm$^3$/g, as determined by mercury porosimetry.

The macroporous crosslinked styrene resin to be used according to the invention is then sulfochlorinated. This is done in a conventional manner, similarly to the reaction of monomeric aromatics, as described, for example, in Houben-Weyl, Methoden der organischen Chemie, volume 9, pages 572–578. Depending on the conditions used, the content of sulfonic acid chloride groups is from 1 to 4.5 milliequivalents/g, preferably from 2 to 4 milliequivalents/g.

Starting from the sulfonic acid chloride groups, the binding groups, and the hydrophilic groups, if any, are next built up. The binding groups serve for covalently binding the proteins whilst the hydrophilic groups impart hydrophilic properties to the carrier and serve to give it an acidic or basic character depending on the proteins used.

As a rule, the binding groups are intended to be able to fix a protein by reacting, at from 0° to 50° C., in aqueous solution, with primary amino groups and/or hydroxyl groups of the proteins, thereby forming a covalent bond to the oxygen or nitrogen atoms of, respectively, the hydroxyl or amino groups of the proteins.

The invention relates to a macroporous polymeric carrier for covalently binding active proteins by means of isocyanate, thioisocyanate or aldehyde groups, and to a process for its preparation, wherein the sulfonic acid chloride groups of a sulfochlorinated macroporous cross-linked styrene resin, containing 1–4.5 milliequivalents/g of sulfonic acid chloride groups and consisting of 50–97% by weight of styrene and 3–50% by weight of divinylbenzene, with or without 1–25% by weight of ethylvinylbenzene and with or without 1–10% by weight, based on the total weight, of a further comonomer are reacted with an α,ω-diamino compound of the formula

H$_2$N—(CH$_2$)$_n$—NH$_2$ where n is a number from 2 to 12, with hydrazine or with an α,ω-diamino-diether of the formula

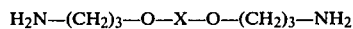
H$_2$N—(CH$_2$)$_3$—O—X—O—(CH$_2$)$_3$—NH$_2$ where X is —(CH$_2$)$_n$—, n being a number from 2 to 6, or where X is a 2,2-dimethyl-1,3-propylene or 3-methyl-1,5-pentylene radical, and any sulfonic acid chloride groups still remaining are hydrolyzed to the free sulfonic acid or saponified to its sodium salt or reacted with a primary or secondary amine to give sulfonamide groups, after which the terminal amino groups from the first process step are reacted with phosgene, thiophosgene, an aliphatic, aromatic or cycloaliphatic diisocyanate or an aliphatic dialdehyde of the formula

OCH—(CH$_2$)$_n$—CHO where n is a number from 1 to 8, to prepare the binding groups.

In the first step of the synthesis of the binding groups, from 10 to 100%, preferably from 10 to 80% and more especially from 10 to 50% of the sulfonic acid chloride groups of the carrier are reacted with an α,ω-diamino compound of the formula

H$_2$N—(CH$_2$)$_n$—NH$_2$ where n is a number from 2 to 12, preferably from 2 to 8, with hydrazine or with an α,ω-diamino-diether of the formula

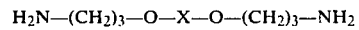
H$_2$N—(CH$_2$)$_3$—O—X—O—(CH$_2$)$_3$—NH$_2$ where X is —(CH$_2$)$_n$—, n being a number from 2 to 6, preferably from 2 to 4, or X is

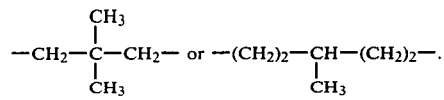
$$—CH_2—\underset{\underset{CH_3}{|}}{\overset{\overset{CH_3}{|}}{C}}—CH_2— \text{ or } —(CH_2)_2—\underset{\underset{CH_3}{|}}{CH}—(CH_2)_2—.$$

This reaction is carried out in the conventional manner. The carrier, in anhydrous dioxane or tetrahydrofuran, is heated with an α,ω-diamino compound or with hydrazine for from 0.5 to 5 hours at from 50° C. to the boiling point of dioxane. During this treatment, the diamino compounds react predominantly monofunctionally so that side groups with terminal amino groups are formed, which at the same time bind the hydrogen chloride liberated. The amount of diamino compound employed depends on the desired degree of conversion. From the point of view of further working up and further reactions it is also possible to use, instead of dioxane and tetrahydrofuran, other water-miscible solvents providing these do not undergo any undesired side reactions with the sulfonic acid chloride groups. Aromatic, cycloaliphatic or aliphatic solvents, for example toluene, cyclohexane or n-octane, can also be used. However, the latter are less advantageous since they are immiscible with water and can therefore only be removed with difficulty from the pores of the carrier.

Subsequently, any sulfonic acid chloride groups which may still remain are hydrolyzed in the conventional manner to the free sulfonic acid or preferably saponified to its sodium salt or converted to a sulfonamide group by reaction with a primary or secondary amine.

The hydrolysis to the sulfonic acid or saponification to the sodium salt is advantageously effected by boiling in water or in very dilute (ie. from about 1 to 4 percent strength by weight) sodium hydroxide solution or sodium carbonate solution. The conversion to the sulfonamide group is advantageously carried out in anhydrous dioxane or tetrahydrofuran, preferably at the boil, the amine being used in excess in order to bind the hydrogen chloride liberated.

The hydrolysis of residual chlorosulfonic acid groups to sulfonic acid groups, or their conversion to sulfonamide groups are particularly advantageous methods of giving the carrier acidic, anion-neutral or basic properties. Advantageous primary or secondary amines to use for the conversion to a sulfonamide are, for example, n-butylamine, di-n-propylamine, diisopropylamine, diisobutylamine, 1,2-dimethylpropylamine, diethylamine, monoethanolamine, diethanolamine and dimethylaminopropylamine, amongst which n-butylamine, di-n-propylamine and dimethylaminopropylamine are preferred.

In the next step, the synthesis of the binding groups is continued by reacting the terminal primary amino groups with phosgene or thiophosgene to give isocyanate or thioisocyanate groups, or reacting them with an aliphatic, aromatic or cycloaliphatic diisocyanate, advantageously with hexane-1,6-diisocyanate, 4,4'-diphenylmethane diisocyanate, toluylene diisocyanate, cyclohexane-1,4-diisocyanate, dicyclohexylmethane diisocyanate or methylcyclohexane diisocyanate or mixtures thereof, or with an aliphatic dialdehyde of the formula

OHC—(CH$_2$)$_n$—CHO where n is a number from 1 to 8, preferably with glutarodialdehyde.

The reaction with phosgene or thiophosgene is advantageously carried out in an inert solvent, especially in toluene, at the boil. The reaction with a diisocyanate is advantageously carried out in anhydrous dioxane or tetrahydrofuran at about 50° C., advantageously in the presence of a catalytic amount of 1,4-diaza-bicyclo(2.2.-2)octane (DABCO).

A particularly preferred diisocyanate is toluylene diisocyanate.

In the reaction with a dialdehyde, the carrier is reacted in an aqueous solution of the dialdehyde at from room temperature to 100° C., preferably from 40° to 100° C. Advantageously, from 2 to 8 moles of dialdehyde are used per equivalent of amino groups to be converted.

In preparing the isocyanate, thioisocyanate or aldehyde groups which act as binding groups, care must of course be taken to exclude undesired side reactions. For example, a diisocyanate should not be used to synthesize the binding groups if the hydrophilic groups have been produced by reaction with an ethanolamine, unless side reactions can be tolerated. On the other hand, for example, there are no objections to the use of a primary amine to prepare the hydrophilic group, if thereafter a thiophosgenation or a reaction with a diisocyanate is carried out (cf. J. Amer. Chem. Soc. 68 (1946), 2,506 or Ann. Chem. 562 (1949), 214).

Preferably, a carrier prepared according to the invention contains from 0.2 to 0.8 milliequivalents of binding groups per gram. The optimum range for a particular purpose can, if necessary, readily be determined from separate experiments.

The carrier according to the invention is charged with a protein by introducing the carrier into an aqueous buffered solution of the protein which is to be bound, at from 0° to 50° C., and stirring the mixture for from 30 minutes to 24 hours. The carrier can also be charged by introducing it into a column through which the buffered protein solution is allowed to flow, or is circulated.

The charged carrier is separated from the solution in the conventional manner and can, for example, be exposed, in the form of a column, to a substrate solution. The preferred conditions for covalently binding a protein are from 0° to 8° C., a pH of from 2 to 10 and a residence time of the aqueous solution of from 1.5 to 5 hours.

Examples of suitable buffers are phosphate buffers, acetate buffers, tris-hydroxymethylaminomethane buffers, ethanolamine buffers, triethanolamine buffers, citrate buffers, borate buffers, glycine buffers, glycylglycine buffers, alanine buffers, glycine-hydrazine buffers and sodium phosphate/semicarbazide buffers.

Preferred suitable enzymes for charging onto, or immobilizing on, the carriers are β-fructosidase, aminoacidacylase, penicillin-acylase and glucose-isomerase.

Further examples of biologically active proteins which can be bound are trypsin, chymotrypsin, pancreatin, α- and β-amylase, ribonucleases, desoxyribonucleases, cellulase, maltase, pectinase, chitinase, pepsin, bromelain, keratinase, amyloglucosidase, lipase, cholinesterase, lecithinase, phosphatase, alginase, asparaginase, glutaminase, urease, lactase, penicillin-amidase, glucose-oxidase, catalase, peroxidase, lipoxidase, xanthin-oxidase, cytochrome-reductase, lactic acid dehydrogenase, collagenase, L-aminoacid-oxidase, D-aminoacid-oxidase, rennin, ficin, subtilisin, tannase, phenyl-oxidase, pullulanase, pancreatin, isoamylase, hexokinase, galactose-oxidase, diaphorase, aldolase, glycolic acid-oxidase, luciferase, aldehyde-oxidase, narringinase, uricase, glutathione-reductase, nitrito-reductase, nitrate-reductase, succinic acid-dehydrogenase and catechol-oxidase.

Preparation of the carrier in the sulfochloride form.

EXAMPLE 1

A suspension comprising 165 g of styrene, 135 g of technical-grade divinylbenzene (containing about 50% of ethylvinylbenzene), 300 g of n-octane, 1.7 g of lauryl peroxide, 1.3 g of polyvinylpyrrolidone as a suspending assistant and 1.1 l of water is stirred under nitrogen for 7 hours at 70° C. and then for 2 hours at 90° C. The resulting macroporous bead polymer, the bead diameters being from 0.2 to 1.5 mm, is washed in methanol and dried at 70° C. under reduced pressure (<30 mbar). Yield: 290.5 g=96.8% of theory.

To convert it to the sulfochloride form, 113 g of the resulting polymer are introduced into 450 ml of chloroform. 300 ml of chlorosulfonic acid are then added dropwise whilst stirring and cooling with ice. The mixture is then stirred for 2 hours at room temperature, followed by 6 hours at the boil. The product is washed first with chloroform and then with dioxane, and is dried at 70° C. under reduced pressure. Yield: 230 g. The content of sulfonic acid chloride groups (determined by titration with N/10 NaOH) is 3.8 milliequivalents/g.

EXAMPLE 2

Carrier containing 4-vinylpyridine as copolymerized units.

This carrier is prepared by a method similar to that of Example 1. 65 g of styrene, 30 g of technical-grade divinylbenzene, 5 g of vinylpyridine, 100 g of n-octane, 3 g of lauryl peroxide, 1.3 g of polyvinylpyrrolidone and 500 ml of water are employed. The polymerization is carried out for 7 hours at 70° C. Yield: 93.5 g=93.5% of theory. Beads having a diameter of 0.2 to 1.5 mm are obtained.

To convert it to the sulfochloride form, 40 g of the resulting polymer are reacted with 120 ml of chlorosulfonic acid in 313 g of chloroform, by a method similar to that of Example 1. Yield: 75 g. The content of sulfonic acid chloride groups (determined by titration with N/10 NaOH) is 4.11 milliequivalents/g.

EXAMPLE 3

Carrier containing hydroxypropyl acrylate as copolymerized units.

This carrier is prepared by a method similar to that of Example 1. 65 g of styrene, 30 g of technical-grade divinylbenzene, 5 g of hydroxypropyl acrylate (a mixture of the 2-hydroxy and 3-hydroxy isomers), 100 g of n-octane, 3.5 g of lauryl peroxide, 1.7 g of polyvinylpyrrolidone and 500 ml of water are employed. The polymerization is carried out for 7 hours at 80° C. Yield: 80.7 g=80.7% of theory. Beads having a diameter of from 0.2 to 1.5 mm are obtained.

To convert the resulting polymer to the sulfochloride form, 40 g of the polymer are reacted with 120 ml of chlorosulfonic acid in 213 g of chloroform. Yield: 67 g. The content of sulfonic acid chloride groups (determined by titration with N/10 NaOH) is 4.0 milliequivalents/g.

Reactions of the chlorosulfonic acid groups with binding and hydrophilic groups.

EXAMPLE 4

30 g of carrier in the sulfochloride form (3.8 milliequivalents/g), as described in Example 1, are treated with 6.6 g of hexane-1,6-diamine in 300 ml of dioxane under reflux for 4 hours, whilst stirring. This converts 50% of the sulfonic acid chloride groups. To saponify the remainder, the polymer is transferred into water, neutralized with sodium bicarbonate and then dried. Yield: 26 g of product wherein the sulfonic acid groups are in the form of the sodium salt.

25 g of the carrier obtained are treated with 200 ml of 25% strength aqueous glutarodialdehyde solution under reflux for 5 hours. The product is then twice stirred for 1 hour in water at room temperature, after which it is dried.

Yield: 30 g.

EXAMPLE 5

70 g of polymer in the sulfochloride form (3.7 milliequivalents/g), as described in Example 1, are stirred with 13 g of hydrazine monohydrate in 200 ml of dioxane for 4 hours at 70° C. This converts 30% of the sulfonic acid chloride groups. For saponification, the carrier is kept in boiling water under reflux for 2 hours, after which it is neutralized with sodium bicarbonate, washed with water and dried.

Yield: 65 g.

30 g of the resulting carrier are stirred with 15.1 g of hexane-1,6-diisocyanate in 200 ml of dioxane for 1 hour at room temperature. 0.5 g of DABCO is then added and the mixture is stirred for 6 hours at 50° C. The carrier is then washed three times with dioxane, freed from the greater part of the solvent by suction filtration, and then lyophilized.

Yield: 32 g.

EXAMPLE 6

25 g of polymer in the sulfochloride form (3.7 milliequivalents/g), as described in Example 1, are treated with 5.4 g of hexane-1,6-diamine in 250 ml of dioxane under reflux for 5 hours, whilst stirring. This converts 50% of the sulfochloride groups. 10.1 g of di-n-propylamine are then added to convert the remaining sulfonic acid chloride groups (the excess amine serves to take up the hydrogen chloride formed), and the mixture is stirred for 5 hours at 60° C. The product is then washed with methanol and water, and is dried.

Yield: 27 g.

25 g of the resulting carrier are treated for 5 hours with 140 ml of 25% strength aqueous glutarodialdehyde solution and 130 ml of water under reflux. The carrier is then stirred with water at room temperature for 1 hour, this treatment is repeated twice, and the product is then dried.

Yield: 26 g.

EXAMPLE 7

70 g of polymer in the sulfochloride form (3.4 milliequivalents/g), as described in Example 1, are treated with 27.8 g of hexane-1,6-diamine in 300 ml of dioxane under reflux for 4 hours in order to convert the sulfonic acid chloride groups completely. The carrier is then kept in water under reflux for 2 hours, after which it is dried.

Yield: 67 g.

30 g of the carrier are treated for 10 hours in a solution of 9.6 g of thiophosgene in 200 ml of toluene under reflux. The product is then treated for 3 hours with 200 ml of toluene and 9.6 g of pyridine under reflux. Thereafter, it is washed with toluene and dioxane, and lyophilized.

Yield: 30.9 g.

EXAMPLE 8

30 g of polymer in the sulfochloride form (4.11 milliequivalents/g), as described in Example 2, are treated with 3.6 g of ethylenediamine in 250 ml of dioxane under reflux for 4 hours, whilst stirring. This converts 50% of the sulfochloride groups. 15.2 g of di-n-propylamine are then added, the excess amine serving to take up the hydrogen chloride formed, and the mixture is refluxed for 4 hours. The product is then washed with methanol and water, and is dried.

Yield: 29 g.

The resulting carrier is stirred with 250 ml of dioxane and 21.5 g of toluylene diisocyanate (a mixture of the 2,4- and 2,6-isomers) for 1 hour at room temperature. 0.5 g of DABCO is then added and the mixture is stirred for 6 hours at 50° C. The carrier is then washed three times with dioxane, freed from the greater part of the solvent by suction filtration, and lyophilized.

Yield 29 g.

EXAMPLE 9

30 g of polymer in the sulfochloride form (4.0 milliequivalents/g), as described in Example 3, are treated with 14.7 g of 4,9-dioxadodecane-1,12-diamine in 250 ml of dioxane under reflux for 4 hours, whilst stirring. This converts 60% of the sulfochloride groups. 11 g of n-butylamine are then added, the excess amine serving to take up the hydrogen chloride formed, and the mixture is stirred for 4 hours at 60° C. The product is then washed with water and dried.

Yield: 34 g.

30 g of the resulting carrier are treated with 250 ml of 16% strength aqueous glutarodialdehyde solution under reflux for 5 hours. The carrier is then stirred in water at room temperature for 1 hour, this treatment is repeated twice, and the product is then dried.

Yield: 37 g.

Charging the carrier with β-fructosidase and aminoacylase, and testing the bound enzyme activity.

EXAMPLE 10

3 g of one of the carriers of Examples 4 to 9 are added to a solution of 450 mg of β-fructosidase or aminoacylase in 90 ml of 0.02 molar potassium phosphate buffer (pH 8 or 7.6). The mixture is then stirred for 2 hours whilst cooling with ice. After 1 hour and after 2 hours, the activity of the carrier-bound material and the residual activity in the solution are determined.

To test the bound β-fructosidase activity in a column (diameter 1.5–2 cm), a nylon net was first introduced into the column. On this was placed a 1–2 cm high layer of silica gel, followed by a 4–5 cm layer of the enzyme-charged carrier. The flow rate of the substrate solution (column volume/h=CV/h) was adjusted so that the reaction being followed (namely the hydrolysis of sucrose) did not take place to the extent of 100%. The substrate solution used was a 40% strength by weight sucrose solution in 0.05 molar sodium acetate buffer (pH 4.65). The degree of hydrolysis was determined polarimetrically.

To test the bound aminoacylase activity, 100 mg of the charged carrier were carefully shaken for 2 minutes at room temperature in 3 ml of 0.1 molar phosphate buffer solution (pH 7.6) containing 10 mg/ml of N-acetyl-D,L-methionine and 0.36 mg of cobalt chloride ($CoCl_2.6\ H_2O$). The amount of L-methionine formed was then found by reaction with L-aminoacid-oxidase and determination of the resulting hydrogen peroxide with peroxidase by UV-spectrophotometric measurement of o-dianisidine (in the oxidized, ie. quinoid, form) (Methods in Enzymology, Vol. II).

The bound enzyme activities are shown in the Table which follows.

$$H_2N-(CH_2)_n-NH_2$$

where n is a number from 2 to 12, with hydrazine or with an α,ω-diamino-diether of the formula $$H_2N-(CH_2)_3-O-X-O-(CH_2)_3-NH_2$$

where X is $-(CH_2)_n-$, n being a number from 2 to 6, or where X is a 2,2-dimethyl-1,3-propylene or 3-methyl-1,5-pentylene radical, and any sulfonic acid chloride groups still remaining are hydrolyzed to the free sulfonic acid or saponified to its sodium salt or reacted with a primary or secondary amine to give sulfonamide groups, after which the terminal amino groups from the first process step are reacted with phosgene, thiophos-

| Carrier Example No. | Synthesis of the binding group | Hydrophilic group | Enzyme | Amount of bound enzyme [mg/g] | Activity | CV/h | Test duration days |
|---|---|---|---|---|---|---|---|
| 4 | hexane-1,6-diamine/ glutarodialdehyde | —SO₃Na (H) | β-fructosidase | 142 | 90%[a] | 3.4 | 8 |
| 5 | hydrazine/hexane-1,6-diisocyanate | —SO₃Na (H) | β-fructosidase | 16.5 | 90%[a] | 1.1 | 7 |
| 6 | hexane-1,6-diamine/ glutarodialdehyde | —SO₂N (Prop)₂ | β-fructosidase | 63 | 80%[a] | 2.4 | 6 |
| 7 | hexane-1,6-diamine/ thiophosgene | —SO₂NH(CH₂)₆NH₂ | β-fructosidase | — | 80%[a] | 1.3 | 4 |
| 8 | ethylenediamine/ toluylene diisocyanate | —SO₂N (Prop)₂ | β-fructosidase | 31.9 | 62%[a] | 1.2 | 6 |
| 9 | 4,9-dioxadodecane-1,12-diamine/ glutarodialdehyde | —SO₂NH But. | β-fructosidase | 12.2 | 58%[a] | 0.9 | 6 |
| 4 | see above | see above | aminoacylase | 118.6 | 1.1 mg[b] | — | — |
| 5 | see above | see above | aminoacylase | 136.6 | 1.2 mg[b] | — | — |

Footnotes to Table
[a] Hydrolysis in %, based on sucrose concentration employed, as described in text.
[b] L-Methionine formed by hydrolysis, as described in text.
CV/h: Column volume/hour.

We claim:
1. A macroporous crosslinked styrene resin, used as a carrier in which a biologically active protein is covalently bound via isocyanate, thiocyanate or aldehyde groups, wherein the sulfonic acid chloride groups of a sulfochlorinated macroporous crosslinked styrene resin, containing 1–4.5 milliequivalents/g of sulfonic acid chloride groups and consisting of 50–97% by weight of styrene and 3–50% by weight of divinylbenzene, with or without 1–25% by weight of ethylvinylbenzene and with or without 1–10% by weight, based on the total weight, of a further comonomer are reacted with an α,ω-diamino compound of the formula gene, an aliphatic, aromatic or cycloaliphatic diisocyanate or an aliphatic dialdehyde of the formula $$OCH-(CH_2)_n-CHO$$

where n is a number from 1 to 8, to prepare the binding groups.

2. A process for fixing proteins wherein a carrier as set forth in claim 1 is stirred with the protein to be bound, in an aqueous solution, at from 0° to 50° C. for from ½ to 24 hours.

3. A process as set forth in claim 2 for fixing β-fructosidase or aminoacid-acylase.

* * * * *